(12) United States Patent
Wylde

(10) Patent No.: US 11,155,745 B2
(45) Date of Patent: Oct. 26, 2021

(54) COMPOSITION AND METHOD FOR SCAVENGING SULFIDES AND MERCAPTANS

(71) Applicant: Clariant International, Ltd., Muttenz (CH)

(72) Inventor: Jonathan James Wylde, The Woodlands, TX (US)

(73) Assignee: Clariant International Ltd., Muttenz (CH)

( * ) Notice: Subject to any disclaimer, the term of this patent is extended or adjusted under 35 U.S.C. 154(b) by 0 days.

(21) Appl. No.: 15/573,783

(22) PCT Filed: Mar. 21, 2016

(86) PCT No.: PCT/EP2016/056118
§ 371 (c)(1),
(2) Date: Nov. 13, 2017

(87) PCT Pub. No.: WO2016/180563
PCT Pub. Date: Nov. 17, 2016

(65) Prior Publication Data
US 2018/0100096 A1    Apr. 12, 2018

Related U.S. Application Data

(63) Continuation of application No. 14/712,547, filed on May 14, 2015, now abandoned.

(30) Foreign Application Priority Data

Jun. 1, 2015 (EP) ..................................... 15170013

(51) Int. Cl.
*C09K 8/532* (2006.01)
*C07C 15/113* (2006.01)
*C07D 255/02* (2006.01)
*C07F 3/06* (2006.01)

(52) U.S. Cl.
CPC ............ *C09K 8/532* (2013.01); *C07C 15/113* (2013.01); *C07D 255/02* (2013.01); *C07F 3/06* (2013.01); *C09K 2208/20* (2013.01); *C09K 2208/32* (2013.01)

(58) Field of Classification Search
CPC ....... C07C 15/113; C07D 255/02; C07F 3/06; C09K 2208/20; C09K 2208/32; C09K 8/532
See application file for complete search history.

(56) References Cited

U.S. PATENT DOCUMENTS

| 3,928,211 | A | 12/1975 | Browning |
| 4,147,212 | A | 4/1979 | Tisdale |
| 4,680,127 | A | 7/1987 | Edmondson |
| 4,839,154 | A * | 6/1989 | Allison ................... C01B 17/00 210/755 |
| 4,978,512 | A | 12/1990 | Thomas |
| 5,128,049 | A | 7/1992 | Gatlin |
| 5,347,004 | A | 9/1994 | Rivers |
| 6,239,081 | B1 | 5/2001 | Korzilius |
| 6,599,472 | B1 | 7/2003 | Hudson |
| 8,512,449 | B1 | 8/2013 | Zaid |
| 2002/0055439 | A1* | 5/2002 | Palmer ................... C09K 8/528 507/200 |
| 2012/0241361 | A1 | 9/2012 | Ramachandran |
| 2013/0004393 | A1 | 1/2013 | Menendez |
| 2013/0023449 | A1 | 1/2013 | Heath |
| 2013/0320258 | A1 | 12/2013 | Lehrer |
| 2014/0057817 | A1 | 2/2014 | Janak |
| 2014/0190870 | A1* | 7/2014 | Lehrer ................... C10G 29/06 208/240 |
| 2014/0231311 | A1* | 8/2014 | Sandu ................... C10G 21/16 208/240 |
| 2015/0001132 | A1 | 1/2015 | Sorrells |
| 2015/0011453 | A1 | 1/2015 | Bennett |
| 2015/0025258 | A1 | 1/2015 | Poland |
| 2015/0080275 | A1* | 3/2015 | Todd ........................ C02F 5/12 507/226 |

FOREIGN PATENT DOCUMENTS

| EP | 0636675 | 2/1995 |
| EP | 2650314 | 10/2013 |

(Continued)

OTHER PUBLICATIONS

"Zinc Hydroxides and Oxides Supported by Organic Ligands: Synthesis and Structural Diversity", Daniel Prochowic, et al., Coordination Chemistry Reviews 270-271 (2-14), pp. 112-126.
International Preliminary Report on Patentability for PCT/EP2016/056118, dated Aug. 25, 2017, 6 pages.

(Continued)

*Primary Examiner* — Alicia Bland
(74) *Attorney, Agent, or Firm* — Tod A. Waldrop

(57) ABSTRACT

This invention relates to a composition comprising 1.) a metal carboxylate, wherein the metal M is selected from the group consisting of Ag, Cn, Hg, Pb, Sn, Ni, Co, Ca, Fe, Zn and Mn, those metals being present as ions in a +2 or +3 charge state, and wherein the carboxylate anion is derived from a hydrocarbyl monocarboxylic acid having 5 to 20 carbon atoms, or a mixture of such acids, 2.) a solvent selected from the group consisting of water, glycol ethers having from 4 to 15 carbon atoms, alkyl alcohols having from 1 to 10 carbons, and aromatic hydrocarbon solvents having from 6 to 30 carbons, and 3.) an emulsion breaker which is a polymeric nonionic surfactant.

20 Claims, No Drawings

(56) References Cited

FOREIGN PATENT DOCUMENTS

| WO | 9802501 | 1/1998 |
| WO | 2013152832 | 10/2013 |
| WO | WO-2013152832 A1 * | 10/2013 |
| WO | 2013181056 | 12/2013 |
| WO | 2014031537 | 2/2014 |
| WO | 2014130503 | 8/2014 |

OTHER PUBLICATIONS

International Search Report for PCT/EP2016/056118, dated May 25, 2016, 2 pages.
OECD 117 Guidelines for the Testing of Chemicals Partition Coefficient (n-octanol/water), High Performance Liquid Chromatography (HPLC) Method, Apr. 13, 2004, 12 pages.

* cited by examiner

COMPOSITION AND METHOD FOR SCAVENGING SULFIDES AND MERCAPTANS

FIELD OF THE INVENTION

The invention relates to a process for scavenging hydrogen sulfide from liquids and/or gas by use of metal carboxylates in combination with a solvating agent and emulsion breaker package as part of a multifunctional formulation. The formulations containing the inventive mixture have particular applicability in scavenging hydrogen sulfide and/or mercaptans yet at the same time prevent the formation of unwanted emulsions and/or deposition of unwanted by-products often associated with using chemistries and/or formulations of the prior art.

BACKGROUND OF THE INVENTION

The presence of sulfhydryl compounds and particularly hydrogen sulfide pose challenges in many industries. Their presence can create a significant health, safety and environmental challenge. There are many different types of sulfhydryl compounds, but the most commonly encountered molecules include hydrogen sulfide ($H_2S$), organo-sulfur compounds containing S—H groups (also called mercaptans), thiol carboxylic acids RC(O)SH, dithio acids RC(S)SH, and related compounds.

In the oil and gas industry the $H_2S$ content of crude oil and natural gas in many areas of the world is high enough to present environmental and safety hazards. Hydrogen sulfide is a flammable, corrosive, and highly toxic gas. $H_2S$ is the most reduced form of sulfur and is produced by sulfate reducing bacteria (SRB) that are often found in the anaerobic conditions encountered in oil reservoirs and is highly soluble in crude oil. As oil is produced, it is depressurized and the $H_2S$ is released and can then be transferred to, for example, oil based drilling fluid during the drilling process and this can become a hazard as the drilling fluid is recirculated from the well to the surface. During the production phase $H_2S$ gas can create a significant integrity risk where it is present at as little as >0.01 psig partial pressure as it is an acid gas and upon dissolving into produced water creates a very corrosive environment and requires to somehow be removed in order for the fluids to be safely processed.

The odor of sulfhydryl compounds is also a challenge in, for example, metal working environments, but equally in water treatment processes, either municipal (e.g. waste water treatment) or industrial (recycling of mining water). SRB are often present in the recirculating fluid systems, and though the bacteria can usually be controlled by the use of biocidal compositions, it is easy to lose control of the biology in the system which results in the production of hazardous $H_2S$ in the system. Furthermore biocides are inefficient at removing $H_2S$ after it forms and only anecdotally scavenge, via either oxidation (e.g. sodium hypochlorite application) or due to the release of low levels of aldehyde during their breakdown (e.g. with glutaraldehyde). Sulfhydryl compounds and particularly $H_2S$ can present environmental, toxicity and integrity challenges in gaseous phases in confined spaces, as for instance in sewage treatment facilities and particularly in shipping and storage containers for moisture sensitive materials that may emit $H_2S$ which can sit in the gaseous headspace. It would be desirable to have a scavenger that could reduce the $H_2S$ concentrations in such locations. It would be particularly advantageous to have such a scavenger that is active in the absence of an aqueous phase. Furthermore it is desirable to have a scavenger that does not produce unwanted by-products or form emulsions that can inadvertently contaminate the very systems they are treating.

A number of methods have been proposed to scavenge hydrogen sulfide and control sulfhydryl odors in hydrocarbon containing systems:

WO-98/02501 describes the use of bisoxazolidines prepared by the reaction of 1, 2 or 1, 3 amino alcohols containing 3 to 7 carbon atoms with aldehydes containing 4 or fewer carbon atoms. The relative oil and water solubility of these products can be controlled through the correct choice of starting materials. These bisoxazolidines react with sulfhydryl compounds present in oil and gas streams to neutralize and therefore scavenge them.

EP-A-2650314 teaches the use of a copolymer, comprising a) 0.1 to 10 mol-%, based on the weight of the copolymer, of structural units derived from vinylphosphonic acid or of a salt thereof, b) 40 to 80 mol-%, based on the weight of the copolymer, of structural units derived from compounds of the formula (1)

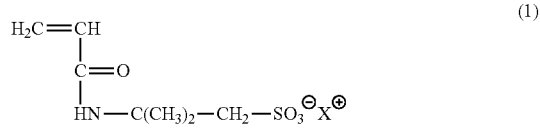

c) 1 to 50 mol-%, based on the weight of the copolymer, of structural units derived from compounds of the formula (5)

in which X is OH or $NR^3R^4$, and $R^3$ and $R^4$, independently of one another, are H or $C_1$-$C_4$-alkyl, for the inhibition and/or dispersion of inorganic sulphide scales.

U.S. Pat. No. 6,239,081 teaches a water-based drilling fluid which comprises at least one alkali metal carboxylate and at least one soluble boron compound. It further relates to the use of boron compounds in drilling fluids which comprise alkali metal carboxylates to decrease the corrosivity of these drilling fluids.

U.S. Pat. No. 5,347,004 teaches the use of reaction products of alkoxyalkylene amine, ammonia, and dialkylamines with aldehydes. These products are used to remove $H_2S$ from gas streams which are sparged into water solutions of the products.

There are multiple patents published in the art that teach the use of triazine chemistry for the control of $H_2S$ in the oilfield environment. U.S. Pat. No. 4,978,512 teaches a method for reducing $H_2S$ and organic sulfides from gaseous and/or liquid hydrocarbon streams by using a reaction product of a lower alkanolamine comprising 1 to about 6 carbons with a lower aldehyde comprising 1 to about 4 carbons. A preferred embodiment is the reaction product of monoethanolamine and formaldehyde which is perhaps one of the most ubiquitously used triazine chemistries in the oil and gas industry today to scavenge $H_2S$.

U.S. Pat. No. 5,128,049 teaches a unique application method for scavenging agents whereby a dilute solution of a scavenging agent, such as triazine, is injected into an $H_2S$ containing fluid, followed by equilibration and a second injection of dilute solution of scavenging agent to further reduce the $H_2S$ content of the treated fluid.

EP-0636675 teaches the further use of a scavenging compound comprising a substantially formaldehyde free 1,3,5-trimethyl-hexahydro-1,3,5-triazine to scavenge gas or liquid hydrocarbon streams containing $H_2S$ and/or mercaptans. The compound described is preferably prepared by the reaction of methylamine and formaldehyde.

U.S. Pat. No. 8,512,449 teaches a method for formulating an oil-soluble triazine sulfide scavenger comprising a liquid sulfide-scavenging composition comprising from about 25 to 80% by volume of a triazine, from about 15 to 50% by volume of a glycol ether, and from about 5 to 40% by volume of an alcohol, with a maximum water content of about 15% by volume, and being oil soluble. The triazine used is a reaction product of a $C_1$ to $C_6$ alkanolamine and a $C_1$ to $C_6$ aldehyde, where the $C_1$ to $C_6$ moiety in each instance is a straight or branched chain alkyl group.

WO-2014/031537 teaches the use of an aldehyde releasing compound, preferably hydantoins, to remove sulfhydryl compounds from hydrocarbon fluids.

U.S. Pat. No. 3,928,211 describes the use of inorganic zinc salts (most preferably zinc carbonate) preferably dispersed into aqueous or non-aqueous oil well drilling fluids with an organic dispersant such as lignin containing materials.

U.S. Pat. No. 4,147,212 teaches the use of a water soluble zinc ammonium carbonate complex used to remove hydrogen sulfide from oils and gases by contact with aqueous solutions of the complex.

U.S. Pat. No. 6,599,472 discloses the use of metal salt carboxylic acids that are soluble in hydrocarbon oils and are used to inactivate odor producing sulfhydryl compounds. Preferred embodiments are zinc neodecanoic acid but equally claimed are carboxylic acids of naphthenic acids, neoacids, isoacids and Guerbet acids and mixtures thereof.

WO-2014/130503 teaches the use of zinc carboxylates, preferably zinc octoate or zinc 2-ethyl hexanoic acid in combination with viscosity improver selected from the group consisting of glycol ethers having from about 4 to about 15 carbon atoms, and/or alkyl alcohols having from about 1 to about 10 carbons, and/or with additional hydrocarbons from about 7 to about 30 carbons. The resultant formulations are used to scavenge hydrogen sulfide gas.

WO-2013/181056 teaches the synergistic hydrogen sulfide scavenging obtained when use of a metal salt, preferably selected from zinc chloride, zinc acetate, zinc octanoate, and zinc salts containing at least one hydrocarbyl group of at least 4 carbon atoms in combination with an oil soluble amine formaldehyde reaction product (triazine).

US-2015/0025258 discloses the use of particulate zinc oxide salts blended in a mixture of two or more carboxylic acids selected from the group consisting of acetic acid, oleic acid, isobutyric acid, lineoleic acid and neodecanoic acid, for the scavenging of hydrogen sulfide.

The object of the invention was to provide formulations which can be used for scavenging of sulfhydryl compounds in crude oil, preferably, but not limited to $H_2S$ and/or mercaptans. The formulations of the invention should have particular applicability in scavenging sulfhydryl compounds and should be notable for improved performance compared to the formulations and chemistries of the prior art.

It has been found that a ternary composition that comprises a metal carboxylate, an organic solvent and an emulsion breaker molecule will scavenge sulfhydryl compounds very effectively, while at the same time not induce any emulsion challenges due to the precipitation of insoluble byproducts. Deposits of sulfide scales can be a significant challenge during the use of metal carboxylate scavengers. Typically carboxylates of zinc are used which results in the deposition of ZnS. This can create significant challenges as ZnS is highly insoluble and can create flow assurance challenges due to blockages in pipes and process equipment as well as exacerbate water in oil emulsions and therefore dehydration of the crude oil.

In a first aspect, the present invention provides a composition, useful as a sulfhydryl scavenger for application in oilfield operations, comprising 1.) a metal carboxylate, wherein the metal M is selected from the group consisting of Ag, Cn, Hg, Pb, Sn, Ni, Co, Ca, Fe, Zn and Mn, those metals being present as ions in a +2 or +3 charge state, and wherein the carboxylate anion is derived from a hydrocarbyl monocarboxylic acid having 5 to 20 carbon atoms, or a mixture of such acids, 2.) a solvent selected from the group consisting of water, glycol ethers having from 4 to 15 carbon atoms, alkyl alcohols having from 1 to 10 carbons, and aromatic hydrocarbon solvents having from 6 to 30 carbons, and 3.) an emulsion breaker which is a polymeric nonionic surfactant.

In a second aspect, the present invention provides the use of the composition of the first aspect as a sulfhydryl scavenger for application in oilfield operations and process systems.

In a third aspect, the present invention provides a process for scavenging sulfhydryl molecules in oilfield operations and process systems, the process comprising adding to a system susceptible to production of sulfhydryl compounds the composition of the first aspect.

In a preferred embodiment, the composition comprises additionally at least one additional hydrogen sulfide scavenger as component from group 4.

In another preferred embodiment, the composition comprises additionally at least one scale inhibitor and/or at least one corrosion inhibitor as component from group 5.

In another preferred embodiment, the composition comprises additionally both at least one additional hydrogen sulfide scavenger as component from group 4 and at least one scale inhibitor and/or at least one corrosion inhibitor as component from group 5.

Group 1

In group 1, the carboxylates are the ones of the metals Ag, Cn, Hg, Pb, Sn, Ni, Co, Ca, Fe, Zn and Mn in their +2 or +3 charge state which means that the metals are present as respectively charged ions.

The compounds of group 1 comprise oil soluble sulfhydryl compound scavengers which in a preferred embodiment are salt compositions of the formula (1)

$$M^{a+}(R-CO_2)_b(OH)_{c-b} \qquad (1)$$

wherein

M is selected from the group consisting of silver, copper, mercury, lead, tin, nickel, cobalt, cadmium, iron and manganese, a is 2 or 3, b is 1, 2 or 3, c is (a-b), and R is a hydrocarbyl radical containing from 4 to 19 carbon atoms, or mixtures of such carboxylates.

The metal ions used to prepare the carboxylate salts of this invention are chosen on the basis that the sulfide salts of the said metal ions are water insoluble or sparingly soluble. Preferably the metal sulfides have solubility in water less than 0.01 wt.-% meaning less than 0.01 g salt/100 cm$^3$ water. The metal sulfides are the sulfides of silver, copper, mercury, lead, tin, nickel, cobalt, cadmium, iron, zinc and manganese. Even more preferred are sulfides of zinc, lead and iron, particularly zinc and iron, and most preferred is zinc sulfide.

The most preferred embodiment for the metal carboxylate is thus a zinc carboxylate. It is known that zinc carboxylates may occur as cyclic structures that correspond to the formula $(Zn)_n(^{-O}{}_2CR)_{(2n-2)}(O)_{[n]/4}$ instead of $Zn(R-CO_2)_b(OH)_{(c-b)}$. Mostly, zinc carboxylate will correspond to the formula $Zn_4(O_2CR)_6O$.

The carboxylic acids used to prepare the compositions of this invention contain from 5 to 20 carbon atoms, and are preferably chosen from those which form oil soluble salts with the metal ions of this invention. The preferred oil solubility is a log Pow of >1 but more preferably >2 where log Pow is measured using the OECD 117 method.

In one preferred embodiment, the acids from which the metal salts of group 1 are formed are liquid below 100° C., more preferably below 50° C., most preferably below 25° C.

In another preferred embodiment, the metal salts according to formula (1) have a viscosity of less than 20,000 cP at standard room temperature and pressure (STP), more preferably below 15,000 cP, most preferably below 10,000 cP. All viscosity measurements were performed at STP using a Brookfield viscometer and a constant rotational speed and spindle type.

The formation of low melting salts typically requires that the carboxylic acids used to synthesize the final product have highly branched structures. Examples of suitable acids include:

Neoacids of the Formula (2)

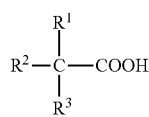

(2)

wherein $R^1$, $R^2$, and $R^3$ are each independently alkyl groups containing 1 to 16 carbon atoms, with the total number of carbon atoms contained in $R^1$, $R^2$, and $R^3$ being from 3 to 18.

Readily available and suitable neoacids include, but are not limited to, neopentanoic acid, neoheptanoic acid, neooctanoic acid, neononanoic acid, neodecanoic acid, and neotridecanoic acid. Neoacids with up to a total average of 20 carbon atoms are also available as mixtures of chain lengths and isomers, and are also suitable, as are mixtures of any of the described neoacids in any proportions. A preferred neoacid is neodecanoic acid as it is readily available and forms low viscosity salts.

2. Isoacids of Formula (3)

$$R^4-CH_2-COOH \qquad (3)$$

wherein $R^4$ is an aliphatic, branched hydrocarbyl group containing from 2 to 20 carbon atoms, wherein branched means that $R^4$ includes at least one methyl group at a position other than the terminal carbon atom.

Readily available isoacids are usually mixtures of isomers which differ in the number and position of the methyl substitutions. Preferred isoacids include isopentanoic acid, isoheptanoic acid, isooctanoic acid, isononanoic acid, isodecanoic acid, and isotridecanoic acid.

3. Guerbet Acids of Formula (4)

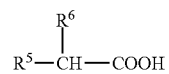

(4)

wherein $R^5$ is a hydrocarbyl group containing from 2 to 8 carbon atoms, and $R^6$ is a hydrocarbyl group containing from 4 to 10 carbon atoms.

Preferred Guerbet acids include 2-ethylhexanoic acid, 2-butyloctanoic acid, 2-hexyldecanoic acid, and 2-octyldodecanoic acid. Most preferred is 2-ethylhexanoic acid.

Group 2

This group comprises hydrocarbon solvents used to deliver the Group 1 metal carboxylate component. The metal carboxylate is delivered as a composition having the metal carboxylate and a solvent. The solvent may be any solvent suitable, for example, for dissolving or suspending the metal carboxylate. In preferred embodiments, the solvent is water, alcohol, a non-alcoholic organic solvent, and/or any combination thereof. The alcohol may include any alcohol suitable as a solvent and for use with oil recovery operations. Preferred are alkyl alcohols having from 1 to 10 carbon atoms, e.g. isopropyl alcohol, methanol, ethanol, propanol, butanol. Another preferred type of alcohols is glycol ethers having from 4 to 15 carbon atoms. Examples of suitable glycol ethers include ethylene glycol, propylene glycol, butylene glycol, oligoethylene glycols, oligopropylene glycols, isopropyl alcohol or any combination thereof. Oligoethylene glycols and oligopropylene glycols preferably have a number average molecular weight between 200 and 1000 g/mol.

According to another preferred embodiment, the organic solvent includes aromatic compounds, either alone or in any combination with the foregoing. In an embodiment, the aromatic compounds have a molecular weight from about 70 to about 400, preferably from about 100 to about 200 g/mol. Examples of suitable aromatic compounds include toluene, xylene, naphthalene, ethylbenzene, trimethylbenzene, and aromatic naphtha (AN), other suitable aromatic compounds, and any combination of the foregoing. It is to be understood that the amount of metal carboxylate in the composition in relation to the solvent may vary in some embodiments depending upon factors such as temperature, time, and type of metal carboxylate. For instance a higher ratio of metal carboxylate to solvent may be used if a faster reaction time is desired.

Group 3

This group comprises emulsion breakers, or demulsifiers or non-emulsifiers. The purpose of having these compounds present is to prevent the formation of emulsions caused by the reaction products of metal carboxylate from Group 1. The metal carboxylate reaction product with sulfhydryl compounds is the corresponding metal sulfide. These metal sulfides are highly oil wetting and as a result they are attracted to the oil/water interface and cause emulsion stability. The purpose of the demulsifier molecule is to break the oil/water emulsion by creating a preferentially water wet surface on the metal sulfide and also to modify the surface tension at the oil/water interface which is stabilized by the metal sulfides to one allowing coalescence of the emulsion.

Examples of suitable polymeric nonionic surfactants include polysorbates, fatty alcohols such as cetyl alcohol and oleyl alcohol, polymers comprising ethylene oxide, polymers comprising propylene oxide, ethylene oxide-propylene oxide copolymers, alkyl polyglucosides such as decyl maltoside, alkylphenol polyethylene oxide, alkyl polyethylene oxide, and ethoxylated and/or propoxylated alkyl phenol-formaldehyde resins.

In preferred embodiments, the emulsion breaker components refer to components or additives that may be added as part of the composition comprising the instant invention and can be described as polymeric nonionic surfactants. Without limitation, examples of suitable polymeric nonionic surfactants include polysorbates, fatty alcohols such as cetyl alcohol and oleyl alcohol, polymers comprising ethylene oxide, polymers comprising propylene oxide, ethylene oxide-propylene oxide copoymers, alkyl polyglucosides such as decyl maltoside, alkylphenol polyethylene oxide, alkyl polyethylene oxide, dodecylbenzenesulfonic acid, and ethoxylated and/or propoxylated alkyl phenol-formaldehyde resins.

In a preferred embodiment, the emulsion breaker is a compound according to the formula (5)

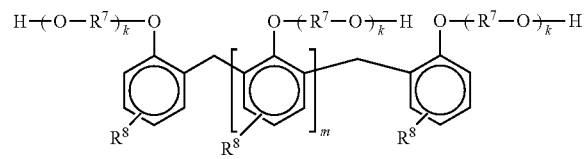

wherein $R^7$ is $C_2$ to $C_4$ alkylene $R^8$ is $C_1$ to $C_{18}$ alkyl k is a number from 1 to 200 m is a number from 1 to 100

In a preferred embodiment $R^7$ is an ethylene or a propylene group. $R^7$ may respect mixtures of different $C_2$ to $C_4$ alkylene groups, preferably ethylene and propylene groups.

In another preferred embodiment, $R^8$ is a $C_4$ to $C_{12}$ alkyl group, more preferably a tertiary butyl group or an iso-nonyl group.

In formula (5), $R^7$, $R^8$ and k may be the same in each of the repeating units, or they may differ from unit to unit.

In another preferred embodiment k is a number from 1 to 20.

In another preferred embodiment m is a number from 3 to 20.

In another specific preferred embodiment the emulsion breaker is dodecylbenzenesulfonic acid:

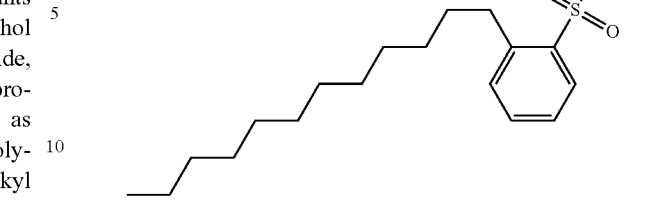

In another preferred embodiment, the demulsifier is a mixture of at least one compound of formula (5) and at least one compound of formula (6). Such mixture preferably contains (5) and (6) in a weight ratio of from 5:1 to 1:5, more preferably in a weight ratio of from 3:1 to 1:3.

The polymeric nonionic surfactant is preferably dissolved or suspended in a solvent. Any solvent suitable for dissolving or suspending a polymeric nonionic surfactant may be used. Examples of suitable solvents include water, butylglycol, ethylene glycol, propylene glycol, butylene glycol, oligoethylene glycols, oligopropylene glycols, ethers, alcohols, toluene, xylene, aromatic naphtha, or any combination thereof. The alcohol may include any alcohol suitable for use with oil recovery and for dissolving the polymeric nonionic surfactant and is preferably selected from the group consisting of isopropyl alcohol, methanol, ethanol, propanol, butanol or any combination thereof.

Group 4

The addition of a further hydrogen sulfide scavenger serves a two-fold purpose. Firstly it scavenges any residual $H_2S$ not scavenged by the Group 1 components, and secondly, there may be a synergy created in scavenging in terms of rate of $H_2S$ uptake.

Additional scavengers that can be included in the formulation include triazine compounds, described by the formula (7):

wherein each $R^9$ is independently selected from the group consisting of $C_1$ to $C_{20}$ straight or branched alkyl groups, or $-R^{10}OH$, where $R^{10}$ is a $C_1$ to $C_{20}$ straight or branched alkylene group. Preferably, at least one $R^9$ group is a $C_1$ to $C_{20}$ straight or branched alkyl group and at least one $R^9$ group is $-R^{10}OH$.

Further, the scavenger can be selected from a range of hemi-acetal compounds, described by the general formula $R^{11}R^{12}C(OH)OR^{13}$ wherein $R^{11}$, $R^{12}$ or $R^{13}$ are hydrogen and/or $C_1$ to $C_{20}$ straight or branched alkyl group. In a preferred embodiment, $R^{11}$, $R^{12}$, $R^{13}$ all are $C_1$ to $C_{20}$ straight or branched alkyl groups.

Further, the scavenger compound may be selected from hydantoins. Exemplary hydantoins include, but are not limited to hydroxyalkylhydantoins, bis(hydroxyalkyl)hydantoins, and dialkylhydantoins, where the alkyl group is generally a $C_1$ to $C_6$ alkyl group. Exemplary hydroxyaklyhydantoins useable as the aldehyde-releasing compound include, but are not limited to, 1-hydroxymethyl-5,5-dimethyl-hydantoin also known as monomethylol-dimethylhydantoin (MDMH), 3-hydroxymethyl-5,5-dimethyl-hydantoin. Exemplary bis(hydroxyl-alkyl) hydantoins useable as the aldehyde-releasing compound include, but are not limited to, 1,3-bis(hydroxymethyl)-5,5-dimethylhydantoin as known as dimethyloldimethylhydantoin (DMDMH). Exemplary dialkylhydantoins useable as the aldehyde-releasing compound include, but are not limited to, 5,5-dimethylhydantoin. In addition, mixtures of the hydantoins may also be used.

Glyoxal (or ethandial) is a dialdehyde that has been shown in the art to scavenge hydrogen sulfide gas (e.g. U.S. Pat. No. 4,680,127) and may also be used in the present invention to scavenge any hydrogen sulfide when contained in a formulation comprising group 1, group 2 and group 3 components.

One preferred embodiment of the current invention is to use 1, 3, 5 Hexahydrotriethanol-1, 3, 5 Triazine to scavenge hydrogen sulfide gas:

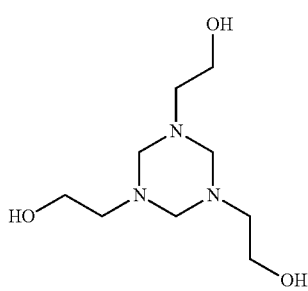

(8)

Another preferred embodiment of the current invention is to use the hemiacetal (ethylenedioxy) dimethanol (EDDM):

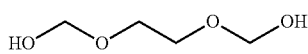

(9)

Yet another preferred embodiment of the current invention is to use 1,3-bis(hydroxymethyl)-5,5-dimethylhydantoin as known as dimethyloldimethylhydantoin (DMDMH):

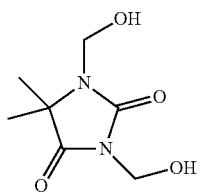

(10)

Group 5

Scale and/or corrosion inhibitors may be added to the target system separately and/or in association with the compounds described in group 1, 2 and 3. The addition of these Group 5 components serves to add functionality to the overall product.

Adding a scale inhibitor can prevent either the deposition of unwanted solids that may result from mixing of incompatible waters. Furthermore, the reaction of metal carboxylates with sulfhydryl compounds very often leads to the precipitation of insoluble sulfide scale, for example the reaction of zinc neodecanoate will inevitably lead to the precipitation of highly water insoluble zinc sulfide.

The corrosion inhibitor serves to reduce the overall corrosivity of the treatment, protecting the tubulars and production equipment that oilfield fluids into which the instant invention is deployed into.

Conventional scale inhibitors which may be added to the water to be treated in conjunction with the present invention include, but are not limited to, 1-hydroxyethane-1,1-diphosphonates, diethylenetriamine penta(methylene phosphonic acid), nitrilo(methylene phosphonic acid), methacrylic diphosphonate homopolymer, polymaleates, polyacrylates, polymethacrylates, polyphosphates, phosphate esters, acrylic acid-allyl ethanolamine diphosphonate copolymer, sodium vinyl sulfonate-acrylic acid-allyl ammonia diphosphonate terpolymer, acrylic acid-maleic acid-diethylene triamine) allyl phosphonate terpolymer and polycarboxylates, all added to the formulation so that the conventional scale inhibitor present in the water to be treated ranges from 20 to 50 mg/L.

Conventional corrosion inhibitors which may be added to the water to be treated in conjunction with the present invention include, but are not limited to soluble zinc salts, nitrates, sulfites, benzoate, tannin, lignin sulfonates, benzotriazoles and mercapto-benzothiazoles amines, imidazolines, quaternary ammonium compounds, resins and phosphate esters, all added to the formulation so that the conventional corrosion inhibitor present in the water to be treated ranges from 50 to 100 mg/L.

One preferred embodiment of the current invention is to use amino tris(methylene phosphonic acid) as scale inhibitor

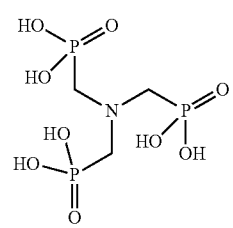

(11)

Another preferred embodiment of the current invention is to use a copolymer, comprising a) 0.1 to 10 mol-% of structural units derived from vinylphosphonic acid and/or of a salt thereof, b) 40 to 90 mol-%, of structural units derived from compounds of the formula (12)

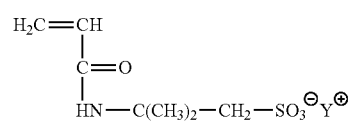

(12)

wherein Y is a cation, preferably selected from the group consisting of $H^+$, alkali metal ions or $NH_4^+$, and c) 1 to 50 mol-% of structural units derived from compounds of the formula (13)

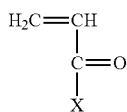

in which

X is OH or $NR^{14}R^{15}$, and $R^{14}$ and $R^{15}$, independently of one another, are H or $C_1$-$C_4$-alkyl.

Molar percentages are to be understood as relating to the total copolymer composition.

In one preferred embodiment, the copolymer comprises additionally 1 to 10 mol-%, based on the total copolymer composition, of structural units of formula (14)

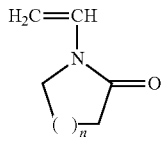

in which n is 1, 2, 3, 4 or 5, preferably 1.

In one preferred embodiment, the copolymer comprises additionally 1 to 10 mol-%, based on the total copolymer composition, of structural units of formula (15)

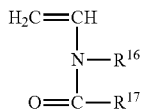

in which $R^{16}$ and $R^{17}$, independently of one another, are hydrogen or $C_1$-$C_4$-alkyl, preferably $R^{16}$ and $R^{17}$ are both hydrogen.

In all embodiments of the invention, monomers comprising an olefinically unsaturated hydrocarbon substituted ammonium salt group, wherein the expression hydrocarbon encompasses groups containing oxygen, are present in the copolymer in an amount of preferably below 1 mol-%, particularly 0.001 to 1 mol-%, especially 0.001 to 0.1 mol-%. They are particularly preferably completely absent.

In all embodiments of the invention, the molar proportion of vinylphosphonic acid or salts thereof is preferably from 0.8 to 6, especially from 1 to 4 mol-%. Suitable salts of vinylphosphonic acid are preferably the alkali metal or ammonium ($NH_4^+$) salts thereof.

In a preferred embodiment, the molar proportion of structural units which are derived from compounds of the formula (12) in all embodiments of the invention is preferably from 45 to 70, especially from 50 to 65 mol-%.

The molar proportion of structural units which are derived from compounds of the formula (13) is preferably from 5 to 45 mol-%, especially from 10 to 40 mol-%. Formula (13) preferably represents acrylic acid and/or acrylamide. If formula (13) represents only acrylamide, the proportion thereof is preferably from 5 to 45 mol-%, especially from 10 to 40 mol-%. If formula (13) represents a mixture of acrylic acid and acrylamide, the proportion of acrylic acid is preferably from 1 to 10 mol-%, especially from 2 to 5 mol-%, and the proportion of acrylamide provides for the difference up to the total molar amount as described above.

The molar proportion of structural units which are derived from compounds of the formula (15) is preferably from 1 to 10 mol-%, particularly from 2 to 8 mol-%, especially from 3 to 7 mol-%.

The molar proportion of structural units which are derived from compounds of the formula (14) is preferably from 1 to 10 mol-%, particularly from 2 to 8 mol-%, especially from 3 to 7 mol-%.

Particular examples of suitable copolymers comprise (molar %).

58% AMPS, 38% Acrylic Amide, 2% n-Vinyl Formamide, 2% Vinyl Phosphonic Acid.

68% AMPS, 28% Acrylic Amide, 2% n-Vinyl Formamide, 2% Vinyl Phosphonic Acid.

83% AMPS, 5% n-Vinyl Pyrrolidone, 5% n-Vinyl Formamide, 5% Acrylic Amide, 2% Vinyl Phosphonic Acid.

The monomer units may be in any sequence in the copolymers. They may be either random polymers or block polymers.

The molecular weights (number average) of the copolymers according to the invention are preferably from 100,000 to 10,000,000 g/mol, in particular from 500,000 to 5,000,000 g/mol. Molecular weight is to be determined by GPC against polyacrylic acid as standard.

The copolymers according to the invention can be prepared by copolymerization of vinyl phoshonic acid and compounds of the formulae (12), (13) and optionally (14), (15) in the stated molar ratios.

The copolymers according to the invention can be prepared by the conventional polymerization methods, such as solution polymerization, mass polymerization, emulsion polymerization, inverse emulsion polymerization, precipitation polymerization or gel polymerization. They are preferably the product of a free-radical copolymerization of vinyl phosphonic acid and the compounds of the formulae (12), (13) and optionally (14), (15).

Yet another preferred embodiment of the current invention is to use tallow alkyl amine ethoxylate as corrosion inhibitor

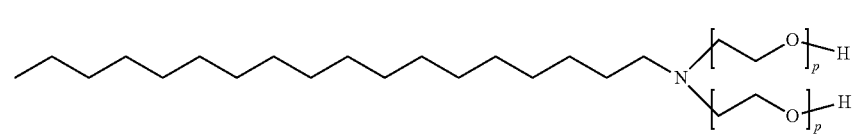

wherein p is a number from 4 to 10.

Yet another preferred embodiment of the current invention is to use coconut alkyl dimethyl benzyl ammonium chloride as corrosion inhibitor

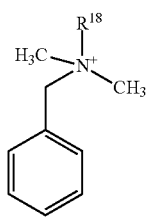

(17)

wherein

R$^{18}$ is C$_8$ to C$_{18}$ alkyl.

The composition may additionally contain biocides, for example, formaldehyde or glutaraldehyde, water dispersants, antifoams, oxygen scavengers and/or flocculants. There may also be added to the water to be treated oxygen scavengers, flocculants such as polyacrylamide dispersants, antifoams such as acetylenic diols, silicones or polyethoxylated antifoams.

The composition of one embodiment of the present invention is preferably prepared by combining:

0.1 to 80 wt.-% of the metal carboxylate species described above in group 1, preferably between 60 and 80 wt.-%, 1 to 50 wt.-% of the solvent species described above in group 2, preferably between 5 and 25 wt.-%, 0.1 to 10 wt.-% of at least one emulsion breaker species described above in group 3, preferably between 0.5 and 2 wt.-%, 1 to 20 wt.-% of the scavenger species described above in Group 4, preferably between 5 and 15 wt.-%, and 0.1 to 5 wt.-% of the scale and/or corrosion inhibitor species described above in Group 6, preferably between 0.2 and 2 wt.-%.

Furthermore, any balance remaining after addition of the 5 components described above is preferably made up with water and/or glycol and/or alcohol based solvents. The alcohols and solvents are preferably selected from, but not limited to, methanol, ethanol, propan-1-ol, propan-2-ol, monoethylene glycol, triethylene glycol, propylene glycol and / or 2-butoxyethanol.

The inventive composition is preferably applied to a production system where significant sulfhydryl compounds are present in concentrations between 0.1 and 10,000 mg/L based on oil production. The exact concentration will preferably depend on the formulation activity itself, the type of sulfhydryl compounds required to be scavenged, static conditions, materials of construction of the medium being treated, quality of the materials being used to make up the inventive solution, temperature of the system and salinity of the system. At this concentration range, the inventive system can provide substantial scavenging of sulfhydryl compounds from the produced liquids in order to maintain the flowability of hydrocarbon production and the quality of the hydrocarbon produced product as it is transported to market.

The present invention also includes a process for applications using the compositions above for application to be deployed in scavenging of sulfhydryl compounds present in the drilling and the production cycle, particularly as a component of well work-over, well intervention, production enhancement and flow assurance packages.

The injection fluid containing the composition of the instant invention may additionally contain other ingredients known to those familiar with the art. Such other ingredients include acids, dispersants, viscosifiers, lubricity agents, scale inhibitors, friction reducers, crosslinker, surfactants, scavenger, pH adjuster, iron control agents, breakers; this is especially true if any produced water (or recycled water) is in contact with the compositions of the instant invention.

Employing the embodiments of the instant invention improves the scavenging of sulfhydryl compounds while not causing formation of complex and difficult to treat emulsions. Furthermore the embodiments of the instant invention will not corrode the oilfield equipment that it comes into contact with, nor will it allow the deposition of unwanted solids, such as metal sulfide scales, so often found with applications of the prior art. Other applications of the embodiments of the instantaneous invention include treating water for downhole injection for pressure support, treatment of drilling and work-over operations, wettability alteration and well cleanout.

EXAMPLES

In the whole specification, all references to percentages are meant to be weight percent relative to the respective whole composition, except if noted otherwise.

Example 1

Scavenger Performance

In order to demonstrate the efficiency of the instant invention in removing sulfhydryl compounds as exhibited by components comprising Group 1, testing was performed focusing on removal of H$_2$S from an oil/water mixture. All testing was performed at 117° F. (47° C.) by sparging 200 ppm and 1,000 ppm H$_2$S gas (in a nitrogen matrix) at 0.15 liters per minute through 300 mL of oil (Eagle Ford condensate) and water (in a 50:50 volume ratio of oil to water) while magnetically stirring at 400 rpm. Five different dose rates of the various scavenger chemicals tested were added to the oil/water mixture at 250, 500, 1,000, 2,000 and 4,000 mg/L.

Efficacy was determined as the time required to measure the same concentration of H$_2$S exiting the test fluid than that entering, i.e. the time required for the scavenger to be 100% spent and loaded with H$_2$S. The longer the time the more efficient the scavenger. The results have been summarized in Table 1.

TABLE 1

H$_2$S scavenger efficiency testing of components that comprise the instant invention and comparative examples from the prior art

| | | 200 ppm H$_2$S (min-sec) | | | 1,000 ppm H$_2$S (min-sec) | |
| --- | --- | --- | --- | --- | --- | --- |
| Example | Chemical | 250 ppm | 500 ppm | 1000 ppm | 2000 ppm | 4000 ppm |
| 1 (C) | 1,3,5 Hexahydrotriethanol-1,3,5 Triazine | 1'50" | 3'42" | 11'22" | 2'12" | 5'17" |

TABLE 1-continued

H$_2$S scavenger efficiency testing of components that comprise the
instant invention and comparative examples from the prior art

| | | 200 ppm H$_2$S (min-sec) | | | 1,000 ppm H$_2$S (min-sec) | |
|---|---|---|---|---|---|---|
| Example | Chemical | 250 ppm | 500 ppm | 1000 ppm | 2000 ppm | 4000 ppm |
| 2 (C) | 1,3,5-trimethylhexahydro-1,3,5-triazine | 1'45" | 3'37" | 11'05" | 2'03" | 5'03" |
| 3 (C) | α,α,α-Trimethyl-1,3,5-triazine-1,3,5(2H,4H,6H)-triethanol | 1'48" | 3'40" | 11'15" | 2'07" | 5'10" |
| 4 (C) | 1,6-dihydroxy-2,5-dioxahexane | 2'15" | 4'58" | 14'24" | 2'44" | 6'31" |
| 5 (C) | 1,3-Dimethylol-5,5-dimethylhydantoin | 2'04" | 4'32" | 12'49" | 2'24" | 5'53" |
| 6 (C) | Zinc neodecanoate | 3'21" | 8'21" | 25'50" | 3'04" | 7'48" |
| 7 (C) | Zinc 2-ethylhexanoate | 3'15" | 8'05" | 24'58" | 2'52" | 7'31" |
| 8 | Instant Invention Formulation | 3'25" | 8'29" | 26'02" | 3'17" | 7'59" |

The inventive formulation of example 8 was as follows: 75% zinc-neodecanoate, 24.3% heavy aromatic naphtha, 0.3% of DDBSA (as described in formula (6)), 0.2% Nonyl acid catalyzed resin with up to 5 mol ethylene oxide (EO) per OH group and an approximate molecular weight of 3,500 g/mol as described in formula (5), and 0.2% Group 5 Copolymer (58% AMPS, 38% Acrylic Amide, 2% n-Vinyl Formamide, 2% Vinyl Phosphonic Acid).

It can be seen that all the triazine compounds that comprised comparative examples 1 (C), 2 (C), and 3 (C) performed very similarly. Comparative examples 4 (C) and 5 (C) performed better than the triazine examples but the raw scavengers of this instant invention in examples 6 and 7 outperformed the comparative examples in terms of H$_2$S loading efficacy.

Example 2

Viscosity Profiles

The purpose of this testing was to determine the effect that Group 2 components had on the viscosity of compositions of the instant invention. Viscosity was measured using a Brookfield viscometer at a constant of 71° F. (22° C.) and ambient pressure. The results have been displayed in Table 2.

TABLE 2

Viscosity measurements of the instant invention and comparative examples

| Example | Chemistry/Formulation | Viscosity (cP) |
|---|---|---|
| 1 (C) | Zinc neodecanoate | 9,000 |
| 2 (C) | Zinc 2-ethylhexanoate | 8,500 |
| 3 (C) | 75% Zinc neodecanoate + 25% MEG | 732 |
| 4 (C) | 75% Zinc 2-ethylhexanoate + 25% MEG | 711 |
| 5 (C) | 75% Zinc neodecanoate + 25% 2-BE | 766 |
| 6 (C) | 75% Zinc 2-ethylhexanoate + 25% 2-BE | 728 |
| 7 (C) | 75% Zinc neodecanoate + 25% HAN | 93 |
| 8 (C) | 75% Zinc 2-ethylhexanoate + 25% HAN | 86 |
| 9 (C) | 75% Zinc neodecanoate + 25% butanol | 624 |
| 10 (C) | 75% Zinc 2-ethylhexanoate + 25% butanol | 586 |
| 11 (C) | 75% Zinc neodecanoate + 25% toluene | 137 |
| 12 (C) | 75% Zinc 2-ethylhexanoate + 25% toluene | 124 |
| 13 | Instant Invention Formulation | 139 |

The inventive formulation of example 13 was 1 as follows: 75% zinc-neodecanoate, 24.3% heavy aromatic naphtha, 0.3% of DDBSA (as described in formula (6)), 0.2% Nonyl acid catalyzed resin with up to 5 mol ethylene oxide (EO) per OH group and an approximate molecular weight of 3,500 g/mol as described in formula (5), and 0.2% Group 5 Copolymer (58% AMPS, 38% Acrylic Amide, 2% n-Vinyl Formamide, 2% Vinyl Phosphonic Acid).

In Table 2 MEG is monoethylene glycol, 2-BE is 2-butoxyethanol, and HAN is heavy aromatic naphtha. It can be seen that viscosity can be dramatically reduced by adding relatively low amounts of solvent compared to the two comparative Group 1 examples. The most effective Group 2 components to add to the Group 1 components for viscosity reduction were heavy aromatic naphtha and/or toluene.

Example 3

Emulsion Testing

It is well known to one skilled in the art that solids in an oil/water mixture can cause significant emulsion stability especially if those solids are liable to oil wet and sit on the oil/water interface. This is the case with zinc sulfide and as this is a reaction product of preferred embodiments of the instant invention, the test work presented here shows how Group 3 emulsion breaker components assist with the resolution of emulsions caused by use of the Group 1 components.

The testing was performed using the standard bottle test, well known to one skilled in the art. This involved taking 100 mL of different ratios of crude oil and synthetic brine in a prescription bottle and agitating them on a mechanical shaker in order to induce emulsions. All tests were performed at a temperature of 140° F. (60° C.) and separation observed for 10 minutes. For tests that contained ZnS, the ZnS was added as a substance in a known concentration. The time taken for emulsion resolution was recorded as water drop rate, crude oil dehydration and interface quality. Water drop rate is the rate at which water volumetrically separates from the crude oil. It is desirable for this to be as quick as possible, achieving a maxima in under 5 minutes is more desirable in oilfield operations. The crude oil dehydration is measured as base sediment and water % (BS&W %) which in this test is the water content that remains in the oil at the end of the test. This gives a secondary indication of performance because while water drop is one desirable feature of a good demulsifier, the remaining water left in the crude oil is ideally <2%, more desirable is <1%. Finally the quality of the interface is important. A clean interface, i.e. a very uniform layer existing between the oil and water, rather than a baggy, or inhomogeneous interface is most desirable. This is because the way oilfield separation process equipment works requires a clean interface to be most efficient. These tests were performed using comparative components and preferred embodiments of the instant invention to show how inclusion of Group 3 components significantly enhanced the resolution of emulsions and that examples from the known art cause substantial challenges with respect to emulsion formation. The results have been summarized in Tables 3 and 4 which show formulations and performance data respectively.

TABLE 3

Formulations tested for emulsion resolution

| Example | Formulation |
|---|---|
| 1 (C) | Zinc-neodecanoate |
| 2 (C) | 75% zinc-neodecanoate, 25% HAN |
| 3 | 75% zinc-neodecanoate, 24% HAN, 1% DDBSA as described in formula (6) |
| 4 | 75% zinc-neodecanoate, 24% HAN, 1% Nonyl acid catalyzed resin with up to 5 mol ethylene oxide (EO) per OH group and an approximate molecular weight of 3,500 g/mol as described in formula (5) |
| 5 | 75% zinc-neodecanoate, 24% HAN, 0.5% DDBSA as described in formula (6) and 0.5% Nonyl acid catalyzed resin with up to 5 mol ethylene oxide (EO) per OH group and an approximate molecular weight of 3,500 g/mol as described in formula (5) |

It can be seen that the presence of ZnS in the oil/water mixtures causes separation issues via emulsion formation. The presence of small concentrations of emulsion breaker bases helps to resolve these emulsions, in Example 5 which is a preferred embodiment of the instant invention, a formulated emulsion breaker package was used to show how complete emulsion resolution can be obtained that could be used as a field solution in order to resolve the challenges caused by the prior art examples.

Example 4

Breakdown Product Inhibition

A further preferred embodiment of the instant invention is to inhibit the formation of undesirable solids. An example is the inhibition of ZnS solids caused by the reaction of preferred embodiments from Group 1 with $H_2S$. Preferred embodiments from Group 5 were included with a preferred embodiment formulation comprising components from Group 1, 2 and 3 and tested for inhibition of undesirable solid formation.

The various formulations were tested at various concentrations in a 50:50 oil/water mixture (as described in Example 1). At the end of the test the total fluids were filtered through a 0.45 pm filter and the solids captured weighted and characterized. A high amount of solids measured indicated poor inhibition of ZnS, and the composition confirmed using x-ray diffraction. The results of this testing has been summarized in Table 5 and 6 which show the formulations tested and performance of these formulations respectively.

TABLE 4

Emulsion resolution testing of the instant invention and comparative examples

| Ex. (from Table 3) | Oil (vol.-%)[1] | ZnS content (wt.-%) | Water Drop (mL) | | | | | | BS&W (%) | Interface Quality |
|---|---|---|---|---|---|---|---|---|---|---|
| | | | 1 min | 2 min | 3 min | 4 min | 5 min | 10 min | | |
| 1 (C) | 50 | 0 | 35 | 41 | 48 | 50 | 50 | 50 | 3.2 | Good, sharp |
| | 50 | 0.5 | 21 | 24 | 27 | 31 | 33 | 41 | 6.3 | Poor, baggy |
| | 70 | 0 | 12 | 18 | 26 | 30 | 30 | 30 | 2.8 | Good, sharp |
| | 70 | 0.5 | 6 | 8 | 10 | 13 | 14 | 19 | 5.9 | Poor, baggy |
| 2 (C) | 50 | 0 | 37 | 42 | 50 | 50 | 50 | 50 | 2.9 | Good, sharp |
| | 50 | 0.5 | 22 | 23 | 29 | 34 | 36 | 44 | 6.1 | Poor, baggy |
| | 70 | 0 | 14 | 19 | 28 | 30 | 30 | 30 | 2.4 | Good, sharp |
| | 70 | 0.5 | 7 | 8 | 12 | 14 | 16 | 21 | 5.7 | Poor, baggy |
| 3 | 50 | 0 | 43 | 48 | 50 | 50 | 50 | 50 | 1.4 | Good, sharp |
| | 50 | 0.5 | 34 | 38 | 42 | 44 | 47 | 50 | 2.3 | Good, sharp |
| | 70 | 0 | 22 | 29 | 30 | 30 | 30 | 30 | 0.9 | Good, sharp |
| | 70 | 0.5 | 16 | 21 | 27 | 29 | 30 | 30 | 1.9 | Good, sharp |
| 4 | 50 | 0 | 42 | 47 | 49 | 50 | 50 | 50 | 1.6 | Good, sharp |
| | 50 | 0.5 | 32 | 36 | 40 | 43 | 46 | 50 | 2.7 | Good, sharp |
| | 70 | 0 | 21 | 28 | 30 | 30 | 30 | 30 | 1.0 | Good, sharp |
| | 70 | 0.5 | 14 | 20 | 26 | 28 | 30 | 30 | 2.1 | Good, sharp |
| 5 | 50 | 0 | 48 | 50 | 50 | 50 | 50 | 50 | 0.3 | Good, sharp |
| | 50 | 0.5 | 46 | 49 | 50 | 50 | 50 | 50 | 0.3 | Good, sharp |
| | 70 | 0 | 27 | 29 | 30 | 30 | 30 | 30 | 0.1 | Good, sharp |
| | 70 | 0.5 | 24 | 28 | 30 | 30 | 30 | 30 | 0.2 | Good, sharp |

[1] The remainder of the 100% is brine

TABLE 5

Formulations tested for ZnS solids deposition potential

| Example | Formulation |
|---|---|
| 1 (C) | Zinc-neodecanoate |
| 2 (C) | 75% zinc-neodecanoate, 25% HAN |
| 3 | 75% zinc-neodecanoate, 24% HAN, 1% DDBSA as described in formula (6) |
| 4 | 75% zinc-neodecanoate, 24% HAN, 1% Nonyl acid catalyzed resin with up to 5 mol ethylene oxide (EO) per OH group as described in formula (5) |
| 5 | 75% zinc-neodecanoate, 24% HAN, 0.5% DDBSA as described in formula (6) and 0.5% Nonyl acid catalyzed resin with up to 5 mol ethylene oxide (EO) per OH group and an approximate molecular weight of 3,500 g/mol as described in formula (5) |
| 6 | 75% zinc-neodecanoate, 24.3% heavy aromatic naphtha, 0.3% of DDBSA (as described in formula (6)), 0.2% Nonyl acid catalyzed resin with up to 5 mol ethylene oxide (EO) per OH group and an approximate molecular weight of 3,500 g/mol as described in formula (5), and 0.2% Group 5 Copolymer (58% AMPS, 38% Acrylic Amide, 2% n-Vinyl Formamide, 2% Vinyl Phosphonic Acid). |

TABLE 6

Results of ZnS solids deposition control

| Example (from table 5) | Table 5 Formulation Concentration (ppm) | Mass of Solids (g) | Composition of Inorganic Component of Solids |
|---|---|---|---|
| 1 (C) | 1,000 | 0.0171 | Zinc sulfide |
|  | 5,000 | 0.0867 | Zinc sulfide |
|  | 10,000 | 0.1682 | Zinc sulfide |
| 2 (C) | 1,000 | 0.0160 | Zinc sulfide |
|  | 5,000 | 0.0649 | Zinc sulfide |
|  | 10,000 | 0.1269 | Zinc sulfide |
| 3 | 1,000 | 0.0127 | Zinc sulfide |
|  | 5,000 | 0.0627 | Zinc sulfide |
|  | 10,000 | 0.1247 | Zinc sulfide |
| 4 | 1,000 | 0.0149 | Zinc sulfide |
|  | 5,000 | 0.0635 | Zinc sulfide |
|  | 10,000 | 0.1245 | Zinc sulfide |
| 5 | 1,000 | 0.0148 | Zinc sulfide |
|  | 5,000 | 0.0630 | Zinc sulfide |
|  | 10,000 | 0.1252 | Zinc sulfide |
| 6 | 1,000 | 0.0027 | Zinc sulfide |
|  | 5,000 | 0.0131 | Zinc sulfide |
|  | 10,000 | 0.03468 | Zinc sulfide |

It can be seen that the amount of zinc sulfide byproduct formed upon sparging through excess H$_2$S in the comparative examples is significant when compared to the inventive example number 6 which shows clear dispersion of ZnS solids.

The invention claimed is:

1. A composition comprising
a metal carboxylate, wherein the metal M is selected from the group consisting of Fe and Zn, those metals being present as ions in a +2 or +3 charge state, and wherein the carboxylate anion is derived from a hydrocarbyl monocarboxylic acid having 5 to 20 carbon atoms, or a mixture of such acids,
a solvent selected from the group consisting of water, glycol ethers having from 4 to 15 carbon atoms, alkyl alcohols having from 1 to 10 carbons, and aromatic hydrocarbon solvents having from 6 to 30 carbons, and
an emulsion breaker which is selected from the group consisting of a polymeric nonionic surfactant and dodecylbenzene sulfonic acid.

2. The composition according to claim 1, wherein the metal carboxylate corresponds to formula (1)

$$M^{a+}(R-CO_2)_b(OH)_{c-b} \tag{1}$$

wherein
M is zinc,
a is 2 or 3,
b is 1, 2 or 3,
c is (a-b), and
R is a hydrocarbyl radical containing from 4 to 19 carbon atoms, or mixtures of such carboxylates.

3. The composition according to claim 1, wherein the metal carboxylate is zinc carboxylate.

4. The composition according to claim 3, wherein the zinc carboxylate corresponds to formula $Zn_4(O_2CR)_6O$, wherein R is a hydrocarbyl radical containing from 4 to 19 carbon atoms, or mixtures of such carboxylates.

5. The composition according to claim 1, wherein the metal carboxylate is oil-soluble.

6. The composition according to claim 1, wherein the acids R—COOH, from which the metal carboxylate is derived, are liquid below 100° C.

7. The composition according to claim 1, wherein M is Fe.

8. The composition according to claim 1, wherein the metal carboxylate of formula (1) is the salt of a neoacid of the formula (2)

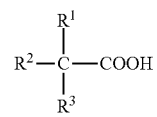

(2)

wherein
R$^1$, R$^2$, and R$^3$ are each independently alkyl groups containing 1 to 16 carbon atoms, with the total number of carbon atoms contained in R$^1$, R$^2$, and R$^3$ being from 3 to 18.

9. The composition according to claim 1, wherein the metal carboxylate of formula (1) is a salt of an isoacid of formula (3)

$$R^4-CH_2-COOH \tag{3}$$

wherein
R$^4$ is an aliphatic, branched hydrocarbyl group containing from 2 to 20 carbon atoms.

10. The composition according to claim 1, wherein the metal carboxylate of formula (1) is a salt of a guerbet acid of formula (4)

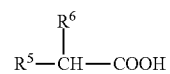

(4)

wherein
R$^5$ is a hydrocarbyl group containing from 2 to 8 carbon atoms, and
R$^6$ is a hydrocarbyl group containing from 4 to 10 carbon atoms.

11. The composition according to claim 1, wherein the solvent is selected from the group consisting of isopropyl alcohol, methanol, ethanol, propanol, butanol. ethylene glycol, propylene glycol, butylene glycol, oligoethylene glycols, oligopropylene glycols, isopropyl alcohol, toluene, xylene, naphthalene, ethylbenzene, trimethylbenzene, and aromatic naphtha (AN).

12. The composition according to claim 1, wherein the emulsion breaker is a compound of formula (5)

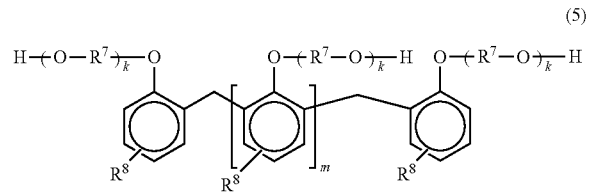

(5)

wherein
$R^7$ is $C_2$ to $C_4$ alkylene
$R^8$ is $C_1$ to $C_{18}$ alkyl
k is a number from 1 to 200 and
m is a number from 1 to 100.

13. The composition according to claim 1, wherein the emulsion breaker is dodecylbenzene sulfonic acid.

14. The composition according to claim 1, further comprising a $H_2S$ scavenger, wherein the $H_2S$ scavenger is a compound selected from the group consisting of triazines according to formula (7)

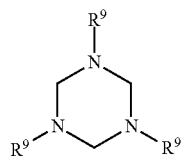

(7)

wherein
each $R^9$ is independently selected from the group consisting of $C_1$ to $C_{20}$ straight or branched alkyl groups, or —$R^{10}$OH, where $R^{10}$ is a $C_1$ to $C_{20}$ straight or branched alkylene group;
hemi-acetal compounds of the general formula $R^{11}R^{12}C(OH)OR^{13}$ wherein $R^{11}$, $R^{12}$ or $R^{13}$ are hydrogen and/or $C_1$ to $C_{20}$ straight or branched alkyl group;
hydroxyalkylhydantoins, bis(hydroxyalkyl)hydantoins, and dialkylhydantoins, wherein the alkyl group is a $C_1$ to $C_6$ alkyl group; and
glyoxal.

15. The composition according to claim 1, further comprising a scale inhibitor selected from the group consisting of 1-hydroxyethane-1,1-diphosphonate, diethylenetriamine penta(methylene phosphonic acid), nitrilo(methylene phosphonic acid), methacrylic diphosphonate homopolymer, polymaleates, polyacrylates, polymethacrylates, polyphosphates, phosphate esters, acrylic acid-allyl ethanolamine diphosphonate copolymer, sodium vinyl sulfonate-acrylic acid-allyl ammonia diphosphonate terpolymer, acrylic acid-maleic acid-diethylene triamine) allyl phosphonate terpolymer and polycarboxylates.

16. The composition according to claim 1, further comprising a scale inhibitor copolymer, wherein the scale inhibitor copolymer comprises
a) 0.1 to 10 mol-% of structural units derived from vinylphosphonic acid and/or of a salt thereof,
b) 40 to 90 mol-%, of structural units derived from compounds of the formula (12)

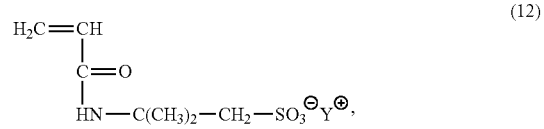

(12)

and
c) 1 to 50 mol-% of structural units derived from compounds of the formula (13)

(13)

in which
X is OH or $NR^{14}R^{15}$, and $R^{14}$ and $R^{15}$, independently of one another, are H or $C_1$-$C_4$-alkyl.

17. The composition according to claim 1, comprising
0.1 to 80 wt.-% of the metal carboxylate,
1 to 50 wt.-% of the solvent, and
0.1 to 10 wt.-% of at least one emulsion breaker.

18. The composition according to claim 14, comprising the $H_2S$ scavenger in an amount of 1 to 20 wt.-%.

19. The composition according to claim 15, comprising the scale inhibitor in an amount of 0.1 to 5 wt.-%.

20. A process for scavenging sulfhydryl molecules in oilfield operations and process systems, the process comprising adding to a system susceptible to production of sulfhydryl compounds the composition according to claim 1.

* * * * *